United States Patent [19]

Ballato

[11] Patent Number: 4,596,697
[45] Date of Patent: Jun. 24, 1986

[54] CHEMICAL SENSOR MATRIX

[75] Inventor: Arthur Ballato, Long Branch, N.J.

[73] Assignee: The United States of America as represented by the Secretary of the Army, Washington, D.C.

[21] Appl. No.: 646,536

[22] Filed: Sep. 4, 1984

[51] Int. Cl.[4] .......................................... G01N 27/00
[52] U.S. Cl. ...................................... 422/98; 422/68; 422/90
[58] Field of Search ........................ 422/61, 68, 69, 88, 422/90, 98; 73/26, 61 R, 579, DIG. 4; 324/56

[56] References Cited

U.S. PATENT DOCUMENTS

| | | | |
|---|---|---|---|
| 4,236,893 | 12/1980 | Rice | 422/61 |
| 4,246,344 | 1/1981 | Silver | 435/39 |
| 4,314,821 | 2/1982 | Rice | 422/61 |
| 4,420,722 | 12/1983 | Todd | 422/98 |

OTHER PUBLICATIONS

W. Shockley et al., "Trapped-Energy Modes in Quartz Filter Crystals", Journal of the Acoustical Soc. of Amer., 1967, pp. 981–993.
"General Relationship of the Thermal Oxidation of Silicon", by B. E. Deal et al., Journal of Applied Physics, 12/65, pp. 3770–3778.

Primary Examiner—S. Leon Bashore
Assistant Examiner—Michael K. Boyer
Attorney, Agent, or Firm—Anthony T. Lane; Jeremiah G. Murray; Roy E. Gordon

[57] ABSTRACT

A chemical sensor matrix is provided for sensing the presence of chemical agents by chemo-electronic means. The chemical sensor matrix is comprised of a plurality of resonators embedded in a single monolithic piece of piezoelectric crystal. The resonators are arranged in rectangular row and column configuration including m rows and n columns, each of the resonators being separated from its neighboring resonators by distances such that the resonant energies do not overlap. Each of the resonators is coated with a different chemical substance to be sensitive to a chemical agent to be detected so that when the chemical substance reacts with the chemical agent, the frequency $f_{mn}$ changes. Each of the rows of resonators bears a metallic electrode stripe for that row, and each of said columns of resonators bears a metallic stripe for that column. The electrode row stripes are positioned on the top surface of the crystal, and the electrode column stripes are positioned on the bottom surface of the crystal. The areas of overlap of said row and column stripes are registered with the central portions of the embedded resonators. Two diode arrays are positioned on the periphery of the crystal for addressing the individual row electrode stripes and the individual column electrode stripes so that the desired resonator can be activated by connecting the stripe corresponding to its row address and the stripe corresponding to its column address to suitable active oscillator circuitry and signal processing means. The resonators $f_{mn}$ can then be interrogated sequentially and frequency change registered.

4 Claims, 3 Drawing Figures

Plan view of entire resonator matrix

Plan view of entire resonator matrix

Individual resonator, plan view, blow-up of one resonator from Figure 1.

CHEMICAL SENSOR MATRIX

The invention described herein may be manufactured, used and licensed by or for the Government for governmental purposes without the payment to me of any royalty thereon. The application is copending with U.S. patent application Ser. No. 639,755 filed Aug. 13, 1984 by Arthur Ballato for "Frequency Synthesizer" and assigned to a common assignee.

This invention relates in general to a chemical sensor and in particular, to a chemical sensor matrix for sensing the presence of chemical agents by chemo-electronic means.

BACKGROUND OF THE INVENTION

The need is well established for being able to sense the presence of chemical agents in many activities as for example, environmental pollution testing and warfare protection. A particular need has arisen for a low cost, small size, light-weight chemical sensor for use on a drone or remotely piloted vehicle for surveying areas of suspected contamination.

SUMMARY OF THE INVENTION

The general object of this invention is to provide a chemical sensor for sensing the presence of chemical agents. A further object of the invention is to provide such a chemical sensor that operates by chemo-electronic means. A still further object of the invention is to provide such a chemical sensor that will have a configuration adaptable for the detection of many chemical agents and that will be small in size, of light weight, and low in cost.

It has now been found that the aforementioned objects can be attained using a bulk acoustic wave (BAW) resonator matrix such as disclosed and claimed in Ser. No. 639,755 by Arthur Ballato for "Frequency Synthesizer" filed Aug. 13, 1984.

More particularly, according to this invention, the chemical sensor matrix is comprised of a plurality of resonators embedded in a single monolithic piece of piezoelectric crystal. The resonators are arranged in rectangular row and column configuration including m rows and n columns the (mn)th resonator having nominal frequency $f_{mn}$, and each of the resonators being separated from its neighboring resonators by distances such that the resonant energies do not overlap. Each of the resonators is coated with a different chemical substance to be sensitive to a chemical agent to be detected so that when the chemical substance reacts with the chemical agent, the frequency $f_{mn}$ changes. Each of the rows of resonators bears a metallic electrode stripe for that row, and each of the columns of resonators bears a metallic electrode stripe for that column. The electrode row stripes are positioned on the top surface of the crystal, and the electrode column stripes are positioned on the bottom surface of the crystal. The areas of overlap of the row and column stripes are registered with the central portions of the embedded resonators. Two diode arrays are positioned on the periphery of the crystal for addressing the individual row electrode stripes and the individual column electrode stripes so that the desired resonator can be activated by connecting the stripe corresponding to its row address and the stripe corresponding to its column address to suitable active oscillator circuitry and signal processing means. The resonators (mn) can then be interrogated sequentially and frequency changes registered.

The chemical sensor matrix is inherently small and can accomodate one hundred or more different types of chemical agents to be detected.

In the frequency sythesizer matrix as disclosed and claimed in Ser. No. 639,755, the frequency associated with the m th row and the n th column of the matrix, is different for each element. In the instant invention, all $f_{mn}$ values may be identical. Manufacturing is thereby made easier.

DESCRIPTION OF THE DRAWING

Referring to FIG. 1, a chemical sensor includes a resonator matrix 10 including a plurality of resonators on a single piece of quartz crystal 12. Each resonator includes a circular, square, or rectangular membrane that has been etched or otherwise cut into the single piece of quartz crystal 12 by methods well recognized in the art. These include photolithography, chemical or ion etching, chemical polishing, etc. The resonators are arranged in a rectangular row and column configuration including m rows and n columns with each of the resonators being separated from its neighboring resonators by such a distance that the resonant energies do not overlap. This is according to well known energy trapping considerations. Such considerations are set forth in the Journal of the Acoustical Society of America, Vol. 41, pages 981 to 993, 1967 by W. Shockley et al. Each of the rows of resonators bears a metallic electrode stripe 16, 18, and 20 for that row. Each of the columns of resonators bears a metallic electrode stripe 22, 24, and 26 for that column. The electrode row stripes 16, 18 and 20 are positioned on the top surface of the crystal and the electrode column stripes 22, 24, and 26 are positioned on the bottom surface of the crystal. The areas of overlap of the row stripes and the column stripes are registered with the central portions of the embedded resonators. Two diode arrays 28 and 30 are positioned on the periphery of the crystal 12 for addressing the individual row electrode stripes 16, 18, and 20 and the individual column electrode stripes 22, 24, and 26 so that the desired resonators can be activated by connecting the stripe corresponding to its row address and the stripe corresponding to its column address to suitable active oscillator circuitry and signal processing means. The resonator (mn) can then be interrogated sequentially and frequency changes registered.

Referring to FIG. 2 and FIG. 3, each resonator is comprised of a thin membrane with top and bottom electrode and coated on the top with a different chemical substance 32 to be sensitive to a chemical agent to be detected so that when the chemical substance 32 reacts with the chemical agent, the frequency $f_{mn}$ changes. The diode array matrix 28, 30 interrogates the resonators (mn) sequentially, and registers the frequencies. Comparison with the $f_{mn}$ starting frequencies, stored in ROM, determines which chemical agents are present, as well as the amount. By storing the results as a function of time, or by using telemetry, the variation of concentration with time can be monitored.

Figure 1:
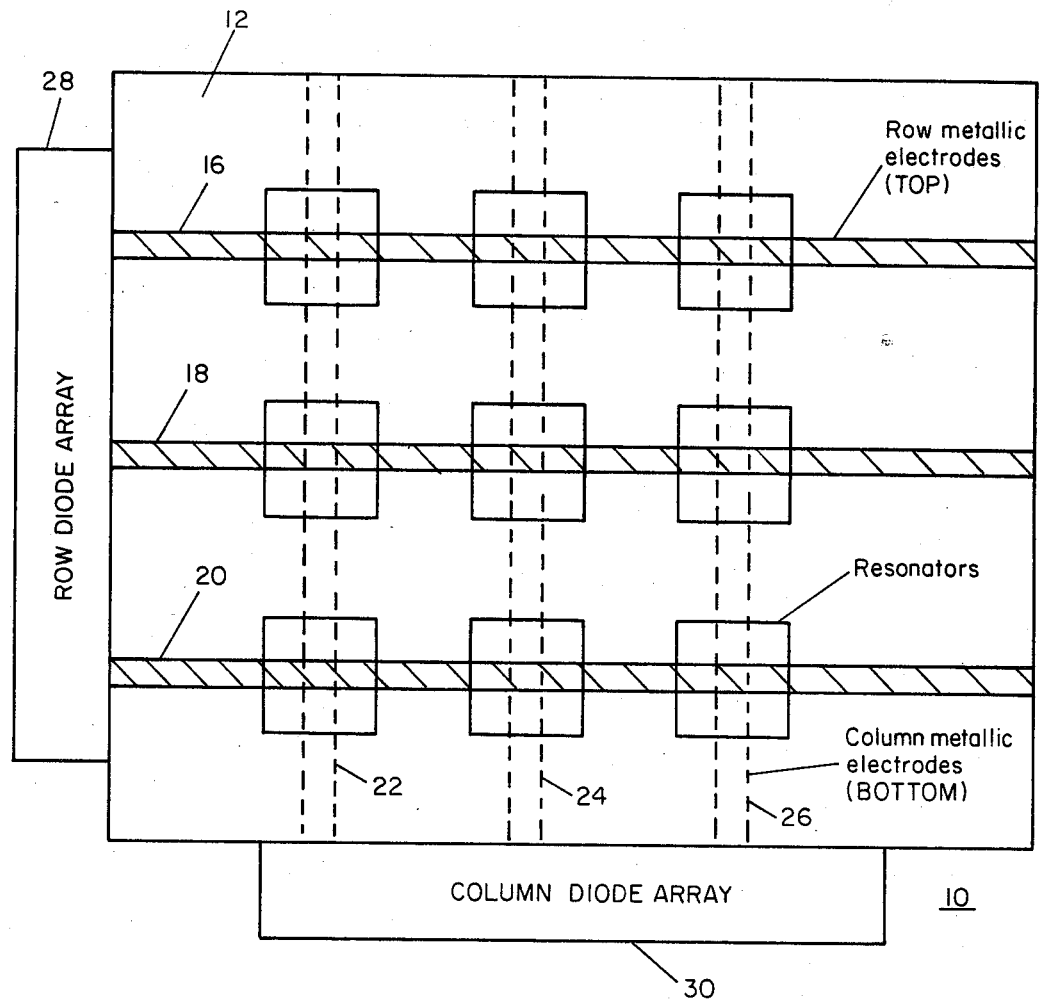
FIG. 1 is a plan view of a resonator matrix array according to the invention including a plurality of resonators embedded in a single monolithic piece of piezoelectric crystal with an electroding arrangement for the resonator matrix and with two diode arrays for addressing individual row electrode stripes and individual column electrode stripes.
Figure 2:
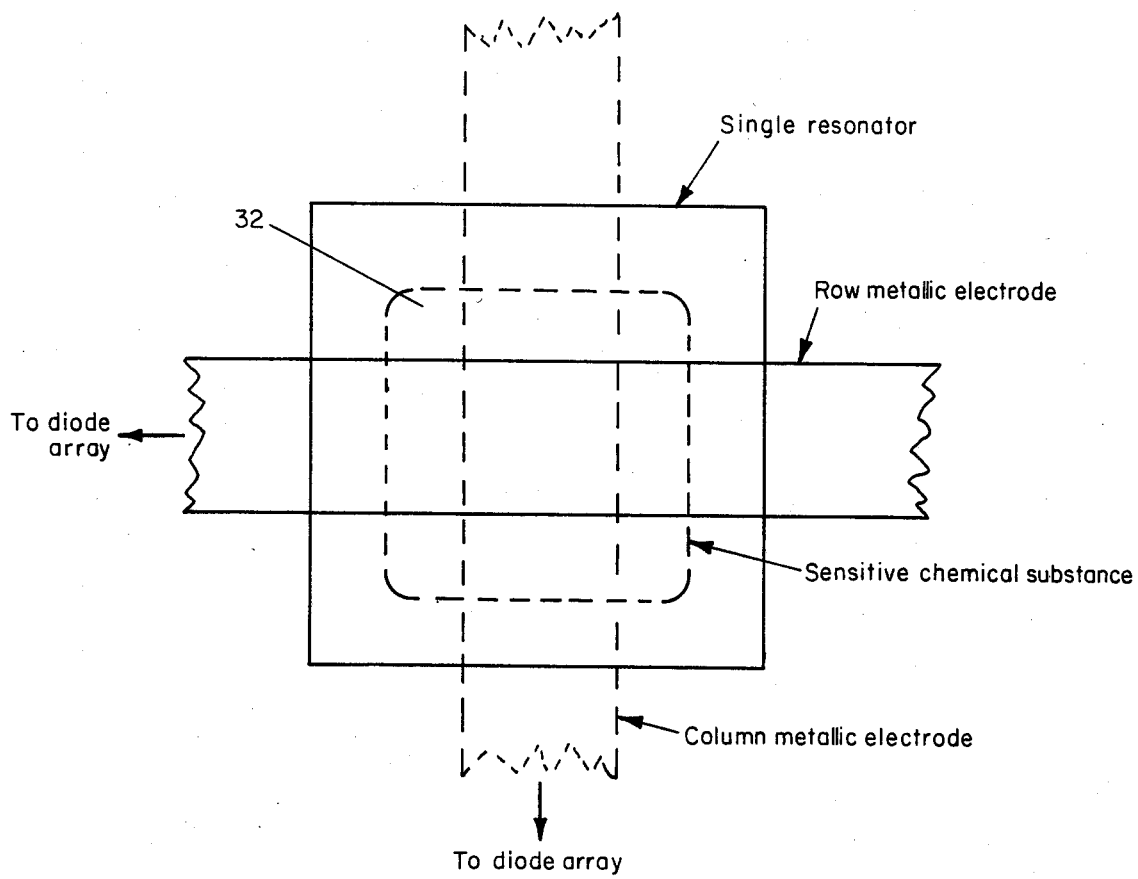
FIG. 2 is a plan view of a blow-up of a single resonator according to the invention.
Figure 3:
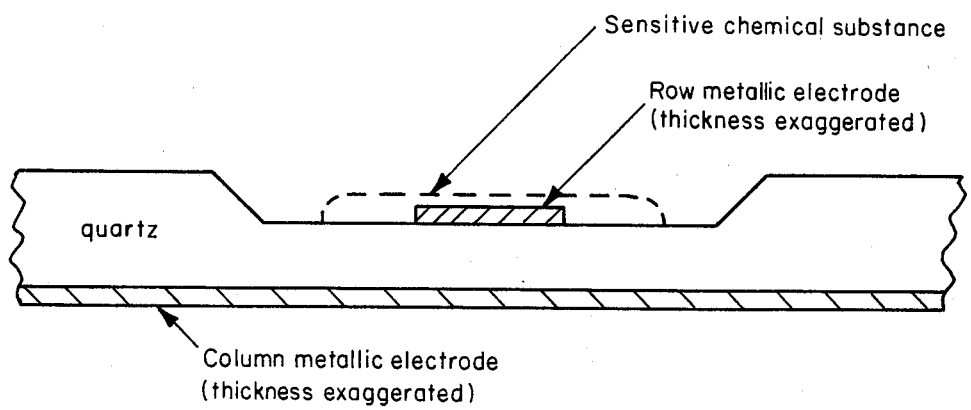
FIG. 3 is a cross sectional view of a blow-up of the single resonator according to the invention.

In some instances it may be difficult to obtain chemical substances that are specific to a single chemical agent, but the presence of many detectors on the array allows one to use several chemical substances, one on each resonator. Each chemical substance might have a different reactivity or sensitivity to the chemical agent being sensed. By putting together the information from the group of sensors, the presence of the suspected chemical agent may be inferred. Using chemical substances on the resonators that operate by absorption, adsorption, desorption or chemical reaction, the individual frequencies may go up or down with exposure.

Though the use of resonators of the same frequencies in the matrix array has been illustrated, the invention also encompasses the use of resonators spaced apart in frequency as in the frequency synthesizer matrix in Ser. No. 639,755.

In lieu of the (BAW) resonator matrix described, one might use a surface acoustic wave (SAW) configuration. In such an instance, the electrode stripes would appear on the same surface and would be parallel. The stripes corresponding to the "row" electrodes would connect to the pin diode array at one side of the matrix, while the "column" electrodes would connect to its diode array at the opposite side of the matrix.

I wish it to be understood that I do not desire to be limited to the exact details of construction as described for obvious modifications will occur to a person skilled in the art.

What is claimed is:

1. A chemical sensor matrix for sensing the presence of chemical agents by chemo-electronic means, said chemical sensor matrix comprising a plurality of resonators embedded in a single monolithic piece of piezoelectric quartz crystal, said resonators being arranged in rectangular row and column configuration including m rows and n columns, each of said resonators being separated from its neighboring resonators by distances such that the resonant energies do not overlap, each of said resonators being coated with a different chemical substance to be sensitive to a chemical agent to be detected so that when the chemical agent reacts with the chemical substance so that the frequency $f_{mn}$ changes, each of said rows bearing a metallic electrode stripe for that row and each of said columns of resonators bearing a metallic electrode stripe for that column, said electrode row stripes being positioned on the top surface of the crystal, said electrode column stripes being positioned on the bottom surface of the crystal, and wherein the areas of overlap of said row and column stripes are registered with the central portions of the embedded resonators, two diode arrays positioned on the periphery of the crystal for addressing the individual row-electrode stripes and the individual column electrode stripes so that the desired resonator can be activated by connecting the stripe corresponding to its row address and the stripe corresponding to its column address to suitable active oscillator circuitry and signal processing means and the resonators (mn) then interrogated sequentially and frequency change registered.

2. A chemical sensor matrix for sensing the presence of chemical agents by chemo-electronic means, said chemical sensor matrix comprising a plurality of resonators embedded in a single monolithic piece of piezoelectric quartz crystal, said resonators being arranged in rectangular row and column configuration including m rows and n columns, each of said resonators being separated from its neighboring resonators by distances such that the resonant energies do not overlap, each of said resonators being coated with a different chemical substance to be sensitive to a chemical agent to be detected so that when the chemical agent reacts with the chemical substance the frequency $f_{mn}$ changes, each of said rows of resonators bearing a metallic electrode stripe for that row and each of said columns of resonators bearing a metallic electrode stripe for that column, said electrode row stripes being positioned on the top surface of the crystal, said electrode column stripes being positioned on the bottom surface of the crystal, and wherein the areas of overlap of said row and column stripes are registered with the central portions of the embedded resonators, two diode arrays positioned on the periphery of the crystal for addressing the individual row electrode stripes and the individual column electrode stripes so that the desired resonator can be activated by connecting the stripe corresponding to its row address and the stripe corresponding to its column address to suitable active oscillator circuitry and signal processing means and the resonators (mn) then interrogated sequentially and frequency change registered and a comparison made with the $f_{mn}$ starting frequencies stored in a read only memory (ROM) device, determining which chemical agents are present, as well as the amount.

3. A chemical sensor matrix according to claim 1 wherein the resonators have the same frequency.

4. A chemical sensor matrix according to claim 1 wherein the resonators differ in frequency.

* * * * *